United States Patent [19]

Pizzino

[11] Patent Number: 4,609,371
[45] Date of Patent: Sep. 2, 1986

[54] DUAL SYRINGE FOR EITHER SIMULTANEOUS OR SEQUENTIAL INJECTION OF LIQUIDS

[76] Inventor: Joanne L. Pizzino, 1426 Sugar Knoll Dr., Akron, Ohio 44313

[21] Appl. No.: 772,060

[22] Filed: Sep. 3, 1985

Related U.S. Application Data

[63] Continuation-in-part of Ser. No. 747,935, Jun. 24, 1985.
[51] Int. Cl.⁴ .............................................. A61M 5/08
[52] U.S. Cl. ................................... 604/191; 604/249
[58] Field of Search .............. 604/191, 187, 80, 81, 604/227, 236, 238, 249, 32

[56] References Cited

U.S. PATENT DOCUMENTS

| | | | |
|---|---|---|---|
| 4,044,757 | 8/1977 | McWhorter et al. | 604/82 |
| 4,109,653 | 8/1978 | Kozam et al. | 604/191 |
| 4,359,049 | 11/1982 | Redl et al. | 604/82 |

FOREIGN PATENT DOCUMENTS 1055518  11/1983  U.S.S.R. .............................. 604/191

*Primary Examiner*—John D. Yasko
*Attorney, Agent, or Firm*—Oldham, Oldham & Weber Co.

[57] ABSTRACT

Dual syringe for either simultaneous or sequential injection of two different injectable liquids. The syringe includes two barrels, each having a plunger for the injection of liquid, and a manually operable three-position rotary valve which controls the filling of the syringe and the outflow of liquid from the syringe. The three positions of the valve permit liquid to be dispensed either from the first barrel only, the second barrel only, or both barrels simultaneously.

3 Claims, 10 Drawing Figures

DUAL SYRINGE FOR EITHER SIMULTANEOUS OR SEQUENTIAL INJECTION OF LIQUIDS

CROSS REFERENCE TO RELATED APPLICATION

This application is a continuation-in-part of applicant's copending application Ser. No. 747,935, filed June 24, 1985.

TECHNICAL FIELD

This invention relates to syringes and particularly to syringes for medical use. More particularly, this invention relates to a novel syringe having two or more barrels which permits the injection of a plurality of liquids into a patient either simultaneously or sequentially.

BACKGROUND ART

Certain patients require the administration of two (and sometimes more) medications in liquid form. Diabetic patients who require two types of insulin, one short acting and the other long acting, are an example. Insulin injection is complicated by the fact that dosage requirements vary from patient to patient and even for the same patient. It is common practice to fill a single syringe with the required amounts of each type of insulin. One procedure presently used for doing this is as follows: the person administering the insulin injects into the first multiple dose vial (Vial #1), which contains one kind of insulin, a volume of air equal to the amount of insulin to be withdrawn from that vial. Then he/she withdraws the required amount of insulin from Vial #1 into the syringe. Then, after removing the needle from Vial #1, the person further withdraws the plunger to fill the syringe with the proper amount of air for injection into Vial #2, which contains a second type of insulin. The person inserts the syringe into Vial #2 and carefully expels the air in the syringe into Vial #2, taking care not to expel the solution from the syringe into Vial #2. Then the person withdraws the plunger, which causes the solution from Vial #2 to be drawn into the syringe. The syringe is then ready for injection. As one can appreciate, it is very difficult to expel the required amount of air in the Vial #2 without also expelling a small amount of insulin from Vial #1. If some insulin from Vial #1 is expelled, of course some insulin from Vial #1 will be introduced into the multiple dose Vial #2 so that Vial #2 no longer contains a pure solution of insulin of the second type. In other words, multiple dose Vial #2 becomes contaminated with insulin of the first type (i.e. from Vial #1) and is no longer pure.

An alternative procedure, seldom used, is simply to inject a solution of insulin of the first type (from Vial #1) from one syringe, then either inject the second type of insulin (from Vial #2) into the patient either using a second syringe or cleaning the first syringe after injection of the first type of insulin but before injection of the second. The alternative procedure has the advantage that neither of the multiple dose vials of insulin will become contaminated with the other type of insulin. It has the obvious and very serious disadvantage of requiring twice as many injections into the patient. Since the frequency of needle injections for diabetic patients is a problem at best, this mode of administration is unacceptable and is therefore seldom used.

The first generally used mode of administration will result in some contamination to at least one of the multiple dose vials of insulin with the other type of insulin unless the person doing the injections is very careful in withdrawing solutions from the respective multiple dose vials. The second mode described above is not widely used because it requires twice as many injections as the first.

DISCLOSURE OF INVENTION

It is an object of this invention to provide a syringe for injection of two different types of medication with a single puncture of the patient's skin and without contamination of either of the multiple dose vials from which the respective injectable liquids are drawn into the syringe.

A further object of this invention is to provide a multiple barrel syringe from which different injectable liquids can be dispensed either one at a time or simultaneously.

This and other objects are accomplished by providing a novel, multiple barrel syringe for injecting a plurality of liquids into a patient either simultaneously or sequentially. This syringe comprises:

a body;

a plurality of barrels in said body, each two said barrels being adapted of contain an injectable liquid;

a plunger in each barrel for injection of said liquids;

a manually operated valve in said body for controlling the dispensing of the respective liquids from said barrels, said valve being arranged so that the liquids may be dispensed either simultaneously or one at a time; and an outlet passage for receiving said liquids.

BEST MODE FOR CARRYING OUT THE INVENTION

This invention will now be described in detail with respect to the preferred embodiment. This preferred embodiment is particularly useful for administering two injectable liquids into a patient where the order in which the two liquids are administered is immaterial. This is the case, for example, when two types of insulin, one short acting and the other long acting, are administered to a patient in order to minimize the fluctuations in blood sugar level during the time between injections. Either type of insulin can be administered first, or both can be administered simultaneously (as is the usual practice); when order of administration is immaterial. This invention will be described with particular reference to a dual syringe for administering both short and long acting insulin, although it will be understood that this type of syringe can be used to administer other pairs of injectable liquids where order of administration is immaterial.

Figure 1:
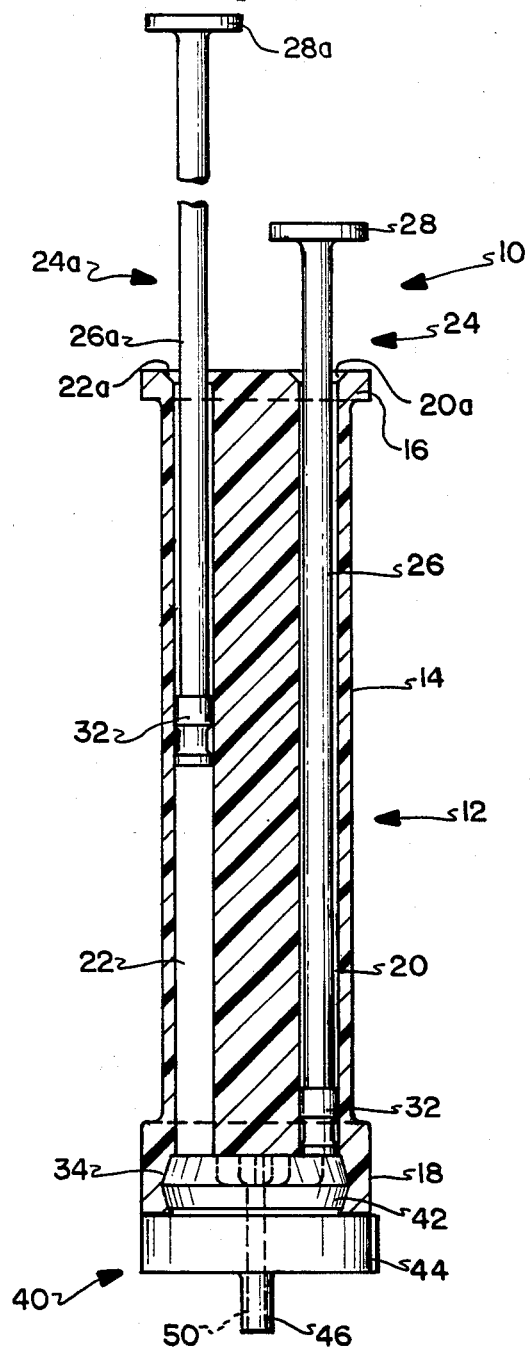
FIG. 1. is a vertical sectional view of a syringe according to the preferred embodiment of this invention.
Figure 4:
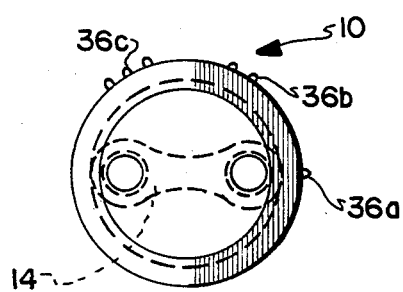
FIG. 4 is a bottom plan view of the syringe body.

Referring now to FIG. 1, 10 indicates generally the preferred syringe according to this invention. Syringe 10 includes a clear plastic syringe body 12 having a cylindrical main portion 14 of dumbbell-shaped cross section, as may be seen in FIG. 4, a round upper flange 16 of short axial length, and a round lower flange 18 which is considerably longer in axial length than the upper flange 16. Syringe body 12 has a pair of longitudinally extending barrels 20,22 of circular cross section. Each of these barrels is adapted to contain a different type of injectable liquid. Thus, for example, barrel 20 may be filled with insulin of one type (say short acting insulin) while the other barrel 22 may be filled with insulin of another type, say for example long acting insulin. Both types may be dissolved in a suitable solvent medium. Each of the barrels may be beveled at the top, i.e. 20a and 22a as shown.

Figure 2A:
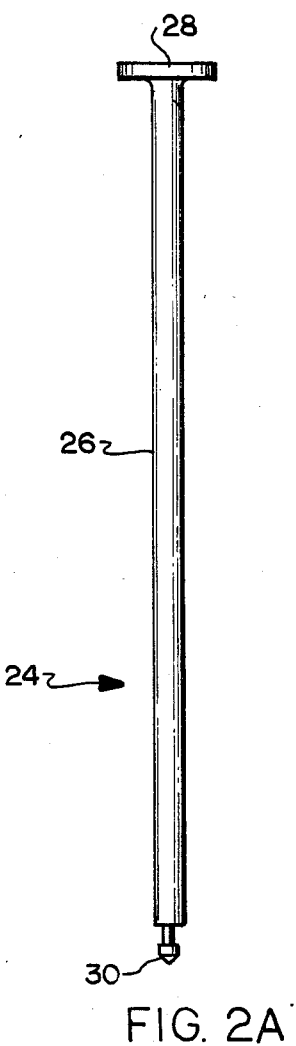
FIGS. 2A and 2B are front elevational views of a plunger for the syringe and a tip for the plunger, respectively.
Figure 2B:

Barrels 20 has a cylindrical plunger 24 which controls the intake and dispensing of liquid medication. Barrel 22 has a plunger 24 which is identical in structure to plunger 24. The structure of plunger 24 is shown best in FIGS. 2A and 2B. Plunger 24 comprises a cylindrical shaft 26, a round head 28 at the top and a pointed tip 30 at the bottom. Plunger 24a has corresponding parts 26a and 28a. Plungers 24, 24a are slightly longer than the respective barrels 20, 20a so that the user can get his/her thumb under thumb pad 26 to lift the plunger. Plungers 24, 24a are preferably made as a unitary device of clear plastic. A rubber tip 32 fits over each plunger tip by snap action.

The lower flange 18 has a cavity 34 of comparatively short axial length and of variable cross section, the widest portion being in the middle. This cavity 34 may comprise two frusta of cones whose bases coincide.

Figure 3:
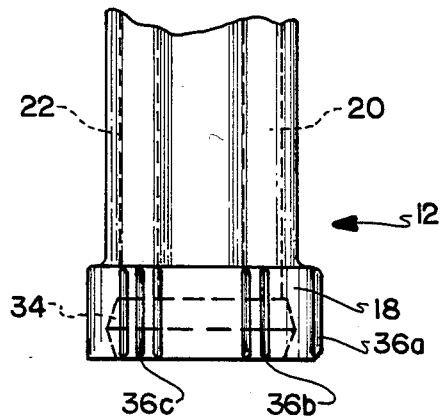
FIG. 3 is a front elevational view of the syringe body.

Flange 18 of syringe body 12 has three sets of markers 36a, 36b, 36c, disposed at intervals of 60°, to denote the position of rotary valve 40. Marker 36a consists of a single longitudinal rib, marker 36b consists of two closely spaced longitudinal ribs, and marker 36c consists of three closely spaced longitudinal ribs. These markers are shown in FIG. 3 but omitted from FIG. 1.

Figure 5:
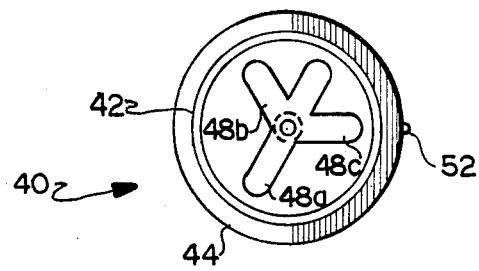
FIG. 5 is a top plan view of the rotary valve which controls outflow of liquids from the syringe.
Figure 6:
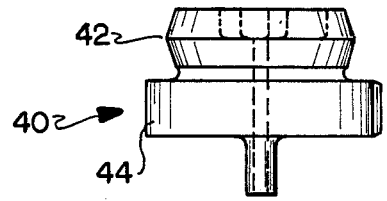
FIG. 6 is a front elevational view of the rotary valve.

Rotary valve 40 will now be described with reference to FIGS. 5 and 6. Referring to FIGS. 5 and 6, rotary valve 40 has, from top to bottom, a convex head 42, a cylindrical portion 44, and a nipple 46, all of which have a common central axis. Head 42 has the shape as recess 34 and fits into recess 34 via snap action. Cylindrical portion 44 has the same diameter as flange 18. Rotary valve 40 includes a diametric open channel 48a and two radial open channels 48b and 48c in the head 42. These form passageways for the outflow of fluids from barrels 20 and 22. As shown in FIG. 5, radial passageways 48b and 48c are disposed at angles of 60° with respect to diametric passage 48a and at an angle of 120° with respect to each other. An axial passage 50 extends along the center axis of rotary valve 40 from passages 48a, 48b and 48c and through nipple 46 to the outside. A needle (not shown) may be inserted into the mouth of passage 50 for injection of fluids from syringe 10 into a patient.

Rotary valve 40 also has a longitudinal rib 52 on the surface of cylindrical portion 44 for denoting the position of rotary valve 40 with respect to syringe body 12. Rib 52 is aligned with passageway 48c.

Rotary valve 40 is preferably made of a clear plastic, but one which is harder than the clear plastic of which syringe body 12 is made. In this manner valve head 42 can be readily inserted into recess 34 and removed therefrom. Valve head 42 engages syringe body 12 in a snap action fit. To assembly syringe 10 for operation, valve head 42 is snapped into place in recess 34 as shown in FIG. 1. After the syringe has been used, valve head 42 may be removed from recess 34 for cleaning of both the syringe body 12 and the rotary valve 40.

Figure 7C:
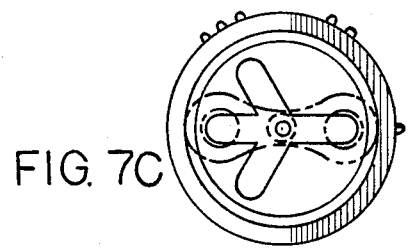
FIGS. 7A, 7B and 7C are diagramatic illustrations of different relative positions of the syringe body and the rotary valve showing how the rotary valve can be turned so as to permit dispensing of liquid from either barrel while the other is closed off, or from both barrels simultaneously.
Figure 7B:
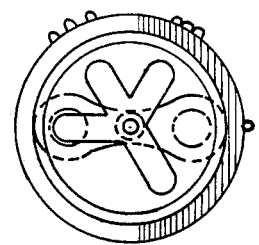

The operation of rotary valve 40 will now be described with reference to FIGS. 7A, 7B and 7C. These three figures show different relative positions of rotary valve 40 with respect to syringe body 12.

Figure 7A:
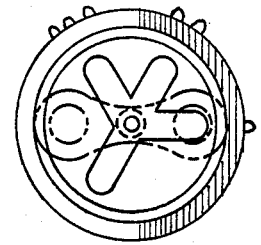

In the first position of rotary valve 40, shown in FIG. 7A, passageway 48c is aligned with the mouth of barrel 20 so that barrel 20 is open, and no passage is aligned with the mouth of barrel 22 so that barrel 22 is closed. Also in this position, rib 52 on rotary valve 40 is aligned with single rib marker 36a. This position permits filling of barrel 20 or dispensing of fluid there-from.

Rotation of rotary valve 40 60° to the left (i.e. counterclockwise) as seen in FIGS. 5 and 7A brings rotary valve 40 to its second position. In this position passageway 48b is aligned with the mouth of barrel 22, barrel 20 is closed, and marker 52 is aligned with double rib marker 36b on syringe body 12. This permits fluids to be exhausted from barrel 22, or to permit filling of barrel 22.

Finally, rotary valve 40 may be rotated a further 60° to the left bringing the two ends of diametric passageway 48a into register with the mouths of barrels 20 and 22, so that both barrels are in communication with outlet passageway 50. This permits dispensing of the liquids in barrels 20 and 22 at the same time. This feature is particularly useful for injecting two kinds of insulin into a patient.

The operation of syringe 10 will now be described in greater detail.

Syringe 10 is ordinarily delivered to the user empty with both plungers 24 down, i.e. in the position of the right hand plunger 24, which is in barrel 20 as shown in FIG. 1.

Syringe 10 may be filled as follows: First, rotary valve 40 is turned to its first position in which barrel 20 is open to outlet passage 50 and barrel 22 is closed. Then the needle (not shown) of syringe 10 is inserted into a first vial (Vial #1) of a first injectable liquid, say a solution of "normal" insulin, and plunger 24 is depressed to expel air into Vial #1, then raised, drawing solution from this vial into barrel 20. Barrel 20 may have graduations (not shown) to indicate the amount of solution in barrel 20 typically expressed as units (when the injectable liquid is insulin). Then, when barrel 20 has been filled to the desired level, the rotary valve 40 is moved to a second position, so that barrel 20 is closed and barrel 22 is open. Then the needle of syringe 10 may be inserted into a second vial (Vial #2), air is expelled into the vial by depressing plunger 24a, and the solution drawn into barrel 22 by raising plunger 24a. Then, with both plungers 24, 24a raised, rotary valve 40 is moved to its third position so that both barrels 20, 22 are open. Then the user presses down simultaneously on the thumb pads 28, 28a of plungers 24, 24a respectively, so that the injectable liquids (say two kinds of insulin solution) are injected into the patient simultaneously.

The syringe 10 of this invention can also be used to inject two liquids sequentially into a patient. This may be done, for example, by filling barrel 22 first and then barrel 20 with the respective injectable liquids, then (while rotary valve 40 is still in its first position) injecting the first liquid from barrel 20 into the patient, then (after rotating valve 40 to its second position) injecting the second liquid from barrel 22 into the patient. The third position of rotary valve 40 (both barrels open) is not used in this mode of operation. This mode of operation is useful when two different liquids must be injected in a predetermined sequence into a patient. This is the situation, for example, when saline solution and heparin solution are injected in that order through a heparin lock in order to maintain patency (openess). Although the syringe of the present invention can be used for injection of two liquids into a patient in predetermined sequence, the preferred syringe for this purpose is that described and claimed in my copending application Ser. No. 747,935, filed June 24, 1985. The disclosure of this earlier application is hereby incorporated by reference.

The syringe of the present invention has a major advantage over the conventional one-barrel syringe when used to inject two liquids at once into a patient. As previously explained, when a conventional syringe is used, there is danger of contamination of the second vial with solution from the first vial when the syringe is being filled with solution from the second vial. This is because it is nearly impossible not to have some solution, no matter how small the quantity, flow from the syringe into the second vial. A further advantage of the dual syringe herein is that it is possible to inject from the syringe into each vial a quantity of air equal to the quantity of solution to be withdrawn. When one uses a conventional one-barrel syringe, one can inject the required amount of air into Vial #1, but it is impossible to inject air into Vial #2 since an attempt to do so would simply expel solution #1 from the syringe into Vial #2. The syringe of the present invention is also advantageous as compared to conventional one-barrel syringes when injecting two different liquids in predetermined sequence into a patient. If one were to inject the two solutions from separate syringes directly into the patient (a seldom used practice), twice as many needle pricks would be required as are necessary when using the dual syringe of the present invention. Use of the syringe of the present invention is also advantageous over use of two separate syringes when in accordance with usual practice liquids are injected through a needle having a heparin lock. It is much more convenient to use a single syringe according to the present invention rather than two syringes. Where the syringe has been prefilled with the two solutions (which may be done when whatever standard quantities of the two injectable liquids are used, as is the case for saline and heparin solutions), the syringe of the present invention offers the further advantage that correct dosage is insured. Use of the syringe of the present invention gives greater assurance that the two liquids will be injected in correct order than is the case when two separate syringes are used. Of course, the syringe of applicant's earlier copending application, Ser. No. 747,935 cited supra is even better than the syringe of the present invention for injecting two liquids in a predetermined order, because the structure of that syringe is such that it is virtually impossible to inject the liquids in the wrong order.

While in accordance with the patent statutes, a preferred embodiment and best mode has been presented, the scope of the invention is not limited thereto, but rather is measured by the scope of the attached claims.

What is claimed is:

1. A syringe for injecting two liquids into a patient, and said syringe comprising:
   a body having two barrels in said body, each of said barrels being adapted to contain an injectable liquid;
   a plunger in each barrel for injection of said liquid;
   an outlet passage for receiving said liquids; and
   a manually operable valve in said body for controlling the dispensing of the respective liquids from said barrels, said valve being selectively movable by the user so that either of said barrels may be placed in communication with said outlet passage while the other barrel is closed, or both barrels are simultaneously in communication with said outlet passage, said valve being movable between first, second and third positions in which one of said barrels, the other barrel, and both barels, respectively, are in communication with said outlet passage.

2. A syringe according to claim 1 in which said valve is a rotary valve.

3. A syringe according to claim 2 in which said outlet passage is in the body of said rotary valve along the center axis thereof.

* * * * *